United States Patent [19]

Haubs et al.

[11] Patent Number: 4,891,135

[45] Date of Patent: Jan. 2, 1990

[54] MACROPOROUS, ASYMMETRIC, HYDROPHILIC POLYARAMIDE MEMBRANE

[75] Inventors: Michael Haubs, Bad Kreuznach; Friedrich Herold, Hofheim; Claus-Peter Krieg, Frankfurt am Main; Detlef Skaletz, Mainz-Bretzenheim; Wildhardt Juergen, Huenstetten, all of Fed. Rep. of Germany

[73] Assignee: Hoechst Aktiengesellschaft, Frankfurt am Main, Fed. Rep. of Germany

[21] Appl. No.: 299,339

[22] Filed: Jan. 23, 1989

[30] Foreign Application Priority Data

Jan. 25, 1988 [DE] Fed. Rep. of Germany ....... 3802030

[51] Int. Cl.$^4$ ...................... B01D 13/00; B01D 13/04
[52] U.S. Cl. .................................. 210/500.38; 264/41
[58] Field of Search ........ 264/212, 41, 45.1, DIG. 62, 264/DIG. 48; 430/110; 210/500.37, 500.38, 500.39

[56] References Cited

U.S. PATENT DOCUMENTS 4,533,616  8/1985  Ohsaki et al. ...................... 430/110
4,752,643  6/1988  Imanishi et al. .................... 264/212

*Primary Examiner*—Frank Sever
*Attorney, Agent, or Firm*—Foley & Lardner, Schwartz, Jeffery, Schwaab, Mack, Blumenthal & Evans

[57] ABSTRACT

A macrophorous, asymmetric, hydrophilic membrane containing polyaramid is described. The characterizing features are that it contains a copolyamide which has at least the following recurring structural units:

(A) —OC—Ar—CO—
(B) —NH—Ar'—NH
(C)

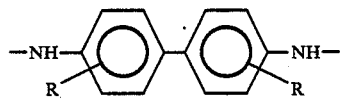

(D)

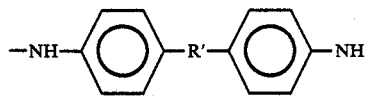

where
Ar and Ar' denote divalent aromatic radicals in which the valence bonds ar in the para or comparable coaxial or parallel position,
denotes a lower alkyl radical or a lower alkoxy radical, in each case having up to 4 carbon atoms, or a halogen radical, and denotes an unsubstituted or substituted methylene radical or an —O—Ar—O— group where Ar has the same structure as given above.

28 Claims, No Drawings

MACROPOROUS, ASYMMETRIC, HYDROPHILIC POLYARAMIDE MEMBRANE

BACKGROUND OF THE INVENTION

The invention relates to macroporous, asymmetric, hydrophilic membranes containing polyaramide and to a process for production of the membranes.

Since the introduction of asymmetric membranes made from cellulose acetate by Loeb and Sourirajan (S. Sourirajan, Reverse Osmosis. Logos Press, London 1970) and made from hydrophobic polymers (U.S. Pat. No. 3,615,024), numerous membranes, in particular for separation of low-molecular-weight and macromolecular components dissolved in water, have been developed and proposed, their structure and suitability have been given in the literature (Desalination, 35 (1980), 5-20) and they have also been successfully tested in industry and for medical purposes.

Many of the membranes described have particularly advantageous properties for achieving specific objectives. As a consequence of their chemical and physical structure, each of the individual membranes can only be optimally suitable for very specific separation problems. This gives rise to the basic need for new membranes for new problems.

EP-A-No. 0,082,433 gives a clear description of the advantages and disadvantages of already known membranes. There are, for example, hydrophilic, asymmetric membranes made from cellulose acetate which have satisfactory anti-absorptive properties, but which leave much to be desired with respect to their thermal and chemical resistance. On the other hand, membranes made from polysulfones or similar polymers have good thermal and chemical resistance, but a pronounced tendency, due to the hydrophobic properties of the polymers employed, to absorb dissolved substances, causing the membrane to become more or less blocked. Although the mixtures of polysulfone and polyvinylpyrrolidone described in EP-A-No. 0,082,433 eliminate the disadvantage caused by the hydrophobicity of the polysulfone, these mixtures are, however, sensitive to exposure to organic solvents.

Hydrophilicity and simultaneous resistance to solvents are found in membranes made from regenerated cellulose. However, these membranes can be hydrolyzed relatively easily in acidic or alkaline media. In addition, they are easily attacked by microorganisms.

SUMMARY OF THE INVENTION

It is therefore an object of the present invention to provide macroporous asymmetric membranes having pronounced hydrophilic properties, i.e., which are capable of absorbing considerable amounts of water, relative to their total weight, are stable to hydrolyzing agents and oxidants and are thermally stable, are more resistant to organic solvents than are membranes made from a hydrophobic polymer, have good wettability, and are also insensitive to the action of microorganisms.

These and other objects are achieved by a membrane comprising a copolyamide having at least the recurring structural units below:

(A) —OC—Ar—CO—
(B) —NH—Ar'—NH—
(C)

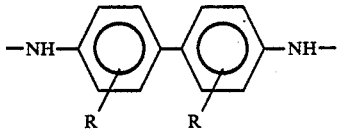

(D)

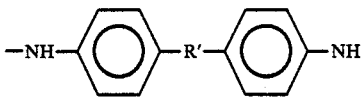

In these formulae,

Ar and Ar' denote divalent aromatic radicals in which the valence bonds are in the para or comparable coaxial or parallel position, R denotes a lower alkyl radical or a lower alkoxy radical, in each case having up to 4 carbon atoms, or a halogen atom, and R' denotes an unsubstituted or substituted methylene radical or an —O—Ar—O— group where Ar has the same structure as indicated above.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

According to the invention, three diamine components are necessary to form the copolyamides present in the membrane. The chain valence bonds on the individual benzene rings should in each case only be in the para position or the corresponding coaxial or parallel position. In order to achieve optimum membrane properties, the concentration of the diamines according to Formula B should be in the range of 5 to 60 mol-%, the concentrations of diamines according to Formula C should be in the range of 5 to 80 mol-%, and the concentrations of the diamines according to Formula D should be in the range of 5 to 50 mol-%, based on 100 mol-% of the acid component according to Formula A that is employed.

The preferred ranges for the concentrations of the diamines are 15 to 50 mol-% for diamine (B), 20 to 75 mol-% for diamine (C) an 10 to 40 mol-% for diamine (D), likewise based on 100 mol-% of the acid component (A) employed.

Compounds that are suitable for the preparation of the copolyamides required according to the invention include the following:

Suitable dicarboxylic acid derivatives of the formula

Cl—CO—Ar—CO—Cl     (A')

are, for example, 4,4,-diphenyl sulfone dicarbonyl dichloride, 4,4'-diphenyl ether dicarbonyl dichloride, 4,4'-diphenyldicarbonyl dichloride and 2,6-naphthalenedicarbonyl dichloride, but very particularly terephthaloyl dichloride.

A suitable aromatic diamine of the structure

  (B')

is, in particular, p-phenylenediamine.

Suitable benzidine derivatives (C') of the formula

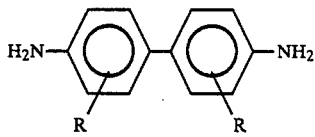

are particularly 3,3'-dimethoxybenzidine, 3,3'-dichlorobenzidine and very particularly 3,3'-dimethylbenzidine.

Of the diamine component (D') of the formula

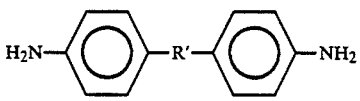

4,4'-diaminodiphenylmethane and 2,2-bis-(4-aminophenyl)-propane may be mentioned particularly and 1,4-bis(4-aminophenoxy)benzene may be mentioned in particular.

The solution condensation of the aromatic dicarboxylic acid dichlorides with the mixtures of aromatic diamines is carried out in aprotic, polar solvents of the amide type, such as, for example, in N,N-dimethylacetamide or in particular in N-methyl-2-pyrrolidone. If appropriate, halide salts from the first and second groups of the periodic table can be added to these solvents in a known manner in order to increase the dissolving power or to stabilize the polyamide solutions. Preferred additives are calcium chloride and/or lithium chloride.

The polycondensation temperatures are usually between $-20°$ C. and $+120°$ C., preferably between $10°$ C. and $100°$ C. Particularly good results are achieved at reaction temperatures between $10°$ C. and $80°$ C. The polycondensation reactions are preferably carried out in a manner such that 2 to 15% by weight, preferably 3.5 to 10% by weight, of polycondensate are present in the solution after completion of the reaction. If, however, the proportion of component "D" approaches 10%, the polymer concentration in the solution must be considerably reduced.

The polycondensation can be terminated in customary manner, for example, by adding monofunctional compounds, such as, for example, benzoyl chloride.

After completion of the polycondensation, i.e., when the polymer solution has reached the Staudinger index necessary for further processing, the hydrogen chloride which has been produced and is loosely bound to the amide solvent is neutralized by addition of basic substances. Examples of suitable substances for this purpose are lithium hydroxide and calcium hydroxide, but in particular calcium oxide.

The Staudinger index is a measure of the mean chain length of the polymers produced.

The Staudinger index of the membrane-forming copolyamides should be between 50 and 1,000 cm$^3$/g, preferably between 100 and 500 cm$^3$/g, particularly preferably between 150 and 350 cm$^3$/g. It was determined on solutions each containing 0.5 g of polymer in 100 ml of 96% strength sulfuric acid at $25°$ C.

The Staudinger index $[\eta]$ (intrinsic viscosity) is taken to mean the term $$\lim_{C_2 \to 0} \frac{\eta_{sp}}{C_2} = [\eta]$$

where $$\eta_{sp} = \text{specific viscosity} = \frac{\eta}{\eta_1} - 1$$

$C_2$ = concentration of the dissolved substance
$\eta$ = viscosity of the solution
$\eta_1$ = viscosity of the pure solvent.

The copolyamides described above are described in DE-A-No. 3,605,394 in connection with moldings. In the present invention they are used to produce a semipermeable macroporous membrane containing the copolyamides as the principal component.

In order to produce the membrane according to the invention from the copolyamides, the above-described solution of the copolyamides is filtered and degassed, and an asymmetric macroporous membrane is then produced in a known manner by phase inversion (Robert E. Kesting, Synthetic Polymeric Membranes, 2nd Ed., 1985, pp. 237 ff.). To this end, the polymer solution is spread as a liquid layer on a substrate which is as level as possible. The planar substrate can comprise, for example, a glass plate or a metal drum.

A precipitation liquid miscible with the solvent of the solution, but in which the polymers dissolved in the polymer solution are precipitated as a membrane, is then allowed to act on the liquid layer. An example of a precipitation liquid is water. Due to the action of the precipitation liquid on the liquid layer comprising the polymer solution, the copolyamides dissolved therein precipitate to form a macroporous film having an asymmetric pore structure.

In carrying out the process, the precipitation liquid is advantageously allowed to act on the membrane precipitated thereby until virtually all the solvent has been replaced by precipitation liquid. The membrane formed is then freed from precipitation liquid, for example by drying the membrane directly in a stream of air or alternatively by first treating the membrane with a plasticizer, such as glycerol, and then drying it.

To produce membranes arranged on a support layer which is permeable to flowable media, the above-mentioned procedures are followed, but a non-woven, for example, of a plastic material, or a paper substrate is used to form the membrane layer. The support serves as a base for the membrane layer which is left on the substrate after formation. However, it is also possible to produce the membrane first without a support and only then to apply it to a permeable support.

Hollow filaments or capillaries can also be produced in a known manner from the solution of the copolyamides by spinning the polymer solution in accordance with the prior art through a shaping annular die or hollow-needle nozzle into the precipitation liquid. The wall thickness of capillaries or hollow fibers of this type is usually in the range 20 to 80 μm.

If the membrane is impregnated with glycerol after coagulation, it can preferably contain in the range from 5 to 60% glycerol, based on its total weight. The membrane impregnated in this way is dried, for example, at a temperature of 50° C.

The membrane according to the invention is also suitable as a support membrane for perm selective layers produced directly on or in the membrane. Thus, for example, "ultrathin" layers ($\leq 1$ μm) made from polymers containing functional groups (for example, silicones, cellulose ethers or fluorinated copolymers) can be spread on water, applied therefrom onto the membrane surface and bound covalently, for example, by reaction with a diisocyanate, in order to achieve higher perm selectivities. Analogously, the membrane according to the invention is also suitable as a support for reactive molecules, for example in order to immobilize enzymes or anticoagulants such as heparin.

The thickness of the membrane according to the invention without a support layer is in the range 10 to 300 μm, in particular 20 to 120 μm.

The invention is described in greater detail with reference to the following illustrative embodiments, which are not limiting. EXAMPLES 1 to 4

In order to produce the membrane investigated in the examples, a copolyamide was produced in N-methylpyrrolidone as solvent from
(A') 100 mol-% of terephthaloyl dichloride (TPC),
(B') 25 mol-% of para-phenylenediamine (PPD),
(C' 50 mol-% of 3,3'-dimethylbenzidine (DMB), and
(D') 25 mol-% of 1,4-bis-(4-aminophenoxy)benzene (BAPOB) at a temperature of 50.C. Solutions of this copolyamide having various Staudinger indices and with various concentrations (Shown in Table 1) were then applied to a non-woven polypropylene support (obtainable from Freudenberg: FO 2430$^{(R)}$ 100 g/m²) using a casting device in accordance with U.S. Pat. No. 4,229,291, and coagulated in water at 14° C. The membranes were then impregnated with an aqueous solution of 40% by weight of glycerol and dried at 50° C. The dry support-reinforced membranes had a thickness of 280 μm.

Surprisingly, the membrane properties can subsequently be modified by heat-treating the membrane. Example 4 demonstrates substantial increases in retention capacity for dissolved substances obtained by placing the membrane in hot water (80° C.).

The membrane properties of the membranes produced in this way are given in Table 1 below.

The Staudinger index was determined in 96% strength $H_2SO_4$ at 25° C. as given in the description.

The mechanical permeability (ultrafiltration) and the retention capacity for dissolved macromolecules were determined in a stirred cylindrical cell (700 rpm, 350 ml, membrane surface area 43 cm²) at pressures of 3.0 bar at 20° C. The retention capacity is defined as $$R = \frac{C_1 - C_2}{C_1} \cdot 100[\%]$$

$C_1$ is the concentration of the aqueous test solution, $C_2$ is the concentration in the permeate.

The test solution employed was a 2% strength aqueous polyvinylpyrrolidone solution (PVP), obtainable under the name "Kollidon K30" ® from BASF, and the molecular weight of the polyvinylpyrrolidone was 49,000 Daltons.

The concentrations were measured in a digital densitometer "DMA 60+601" ® from Heraeus.

TABLE 1

| Example | TPC (Mol-%) | PPD (Mol-%) | BAPOB (Mol-%) | DMB (Mol-%) | CaCl$_2$ PW$^1$ | Staudinger index (cm³/g) | Polymer concentration (%) | Mechanical permeability (l/m²h) | Retention capacity (%) | Test substance |
|---|---|---|---|---|---|---|---|---|---|---|
| 1 | 100 | 25 | 25 | 50 | 3.0 | 188 | 7.0 | 97.5 | 92 | PVP K30 |
| 2 | 100 | 25 | 25 | 50 | 3.0 | 328 | 6.0 | 306 | 75 | PVP K30 |
| 3 | 100 | 25 | 25 | 50 | 3.0 | 188 | 4.67 | 216 | 85 | PVP K30 |
| 4$^2$ | 100 | 25 | 25 | 50 | 3.0 | 188 | 7.0 | 63 | 99.5 | PVP K30 |
|  |  |  |  |  |  |  |  |  | 99.0 | PEG$^3$ 10,000 |

$^1$Parts by weight, based on 100 parts by weight of the polymer solution
$^2$Thermal aftertreatment of the membranes from Example 3: 48 hours, 80° C. in water
$^3$Polyethylene glycol, molecular weight 10,000

EXAMPLES 5 to 9

In order to test the solvent resistance of membranes according to the invention, the membranes of Examples 1 to 4 were placed in acetone for 1 hour in order to replace the liquid present in the membrane pores by acetone. The membranes were then exposed to the solvents given in Table 2 for a period of 12 hours at a temperature of 25° C. The membranes were then reconditioned to water, and the mechanical permeability and retention capacity of the membranes treated with the organic solvents were measured as stated under Example 1. The results are given in Table 2 and show that the differences from the values given in Table 1 are within the tolerance limits of the measurement method.

TABLE 2

| Example | Membrane from Example | Solvent | Mech. permeability (l/m²h) | Retention capacity (%) | Test substance |
|---|---|---|---|---|---|
| 5 | 1 | THF$^1$ | 92.3 | 93 | PVP K30 |
| 6 | 1 | CH$_2$Cl$_2$ | 90.5 | 92.5 | PVP K30 |
| 7 | 2 | CHCl$_3$ | 301 | 76 | PVP K30 |
| 8 | 2 | Toluene | 288 | 75.5 | PVP K30 |
| 9 | 3 | EA$^2$ | 199 | 86.5 | PVP K30 |

$^1$Tetrahydrofuran
$^2$Ethyl acetate

What is claimed is:

1. A macroporous, asymmetric, hydrophilic membrane, comprising polyaramid comprising a copolyamide having at least the following recurring structural units:
(A) —OC—Ar—CO—
(B) —NH—Ar'—NH
(C)

(D)

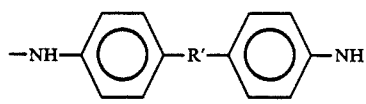

where
Ar and Ar' denote divalent aromatic radicals in which the valence bonds are in the para or comparable coaxial or parallel position,
R denotes a lower alkyl radical or a lower alkoxy radical in each case having up to 4 carbon atoms, or a halogen radical, and
R' denotes an unsubstituted or substituted methylene radical or an —O—Ar—O— group where Ar has the structure as given above.

2. A membrane as claimed in claim 1, wherein the concentration of the diamine components (B) is in the range of 5 to 60 mol-%, the concentration of the diamine component (C) is in the range of 5 to 80 mol-% and the concentration of the diamine component (D) is in the range 5 to 50 mol-%, based on 100 mol-% of the acid component (A).

3. A membrane as claimed in claim 1, wherein the concentration of the diamine component (B) is 15 to 50 mol-%, the concentration of the diamine component (C) is 20 to 75 mol-% and the concentration of the diamine component (D) is 10 to 40 mol-%, based on 100 mol-% of the acid component (A).

4. A membrane as claimed in claim 1, wherein component (A) is selected from the group consisting of 4,4'-diphenyl sulfone dicarbonyl dichloride, 4,4'-diphenyl ether dicarbonyl dichloride, 4,4'-diphenyldicarbonyl dichloride, 2,6-naphthalenedicarbonyl dichloride, and terephthaloyl dichloride.

5. A membrane as claimed in claim 1, wherein diamine component (B) is, p-phenylenediamine.

6. A membrane as claimed in claim 1, wherein diamine component (C) is selected from the group consisting of 3,3'-dimethoxybenzidine, 3,3'-dichlorobenzidine and 3,3'-dimethylbenzidine.

7. A membrane as claimed in claim 1, wherein diamine component (D) is selected from the group consisting of 4,4'-diaminodiphenylmethane, 2,2-bis(4-aminophenyl)propane and very particularly 1,4-bis(4-aminophenoxy)benzene.

8. A membrane as claimed in claim 1, wherein the copolyamide has a Staudinger index in the range from 50 to 1,000 cm$^3$/g, measured in 96% strength of sulfuric acid at 20° C.

9. A membrane as claimed in claim 1, comprising a flat membrane having a thickness in the range 10 to 300 μm.

10. A membrane as claimed in claim 9, additionally comprising a support layer permeable to flowable media that is made from a plastic nonwoven or paper.

11. A membrane as claimed in claim 1, wherein the membrane is a hollow fiber membrane.

12. A membrane as claimed in claim 1, containing 5 to 60% by weight of glycerol, based on the total weight of the membrane.

13. A process for the production of a macroporous, asymmetric, hydrophilic membrane, comprising polyaramid comprising a copolyamide having at least the following recurring structural units:
(A) —OC—Ar—CO—
(B) —NH—Ar'—NH—
(C)

(D)

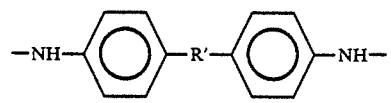

where
Ar and Ar' denote divalent aromatic radicals in which the valence bonds are in the para or comparable coaxial or parallel position,
R denotes a lower alkyl radical or a lower alkoxy radical in each case having up to 4 carbon atoms, or a halogen radical, and
R' denoted an unsubstituted or substituted methylene radical or an —O—Ar—O— group where Ar has the structure as given above,
comprising the steps of:
spreading a layer of a solution comprising the copolyamide and an aprotic, polar amide solvent on a planar substrate;
applying a precipitation liquid miscible with the aprotic, polar amide solvent to the layer; and
precipitating the copolyamide as a membrane.

14. The process as claimed in claim 13, wherein the precipitation liquid used is water.

15. The process as claimed in claim 13, wherein the precipitation liquid is allowed to act on the membrane precipitated until virtually all the solvent has been replaced by precipitation liquid.

16. A process for modifying the retention capacity of a membrane produced as claimed in claim 15 comprising the step of subjecting the membrane to heat treatment in a liquid.

17. The process as claimed in claim 16, wherein the heat treatment is carried out in an inert liquid.

18. The process as claimed in claim 16, wherein the heat treatment is carried out at a temperature in the range from 60° to 220° C. over a period of 0.1 to 96 hours.

19. A process for modifying the retention capacity of a membrane produced as claimed in which a membrane as claimed in claim 15, which comprising the step of subjecting the membrane, to heat treatment with steam.

20. The process as claimed in claim 13, additionally comprising the step of drying the membrane in a stream of air.

21. The process as claimed in claim 20, additionally comprising the step of treating the membrane before drying with a plasticizer.

22. A process for modifying the retention capacity of a membrane produced as claimed in claim 21, comprising the step of subjecting the membrane to heat treatment in warm air of relative atmospheric humidity 20 to 100%.

23. The process as claimed in claim 20, wherein the membrane is dried at a temperature of 50° C.

24. A process as claimed in claim 13, wherein the copolyamide has a Staudinger index in the range from 100 to 500 $cm^3/g$.

25. A process as claimed in claim 13, wherein the copolyamide has a Staudinger index in the range from 150 to 350 $cm^3/g$.

26. A process as claimed in claim 13, wherein the thickness is in the range of 20 to 150 $\mu m$.

27. A process as claimed in claim 13, wherein the amide solvent comprises N,N-dimethylacetamide.

28. A process as claimed in claim 13, wherein the amide solvent comprises N-methyl-2-pyrrolidone.

* * * * *